US005750828A

United States Patent [19]

Eubanks

[11] Patent Number: 5,750,828
[45] Date of Patent: *May 12, 1998

[54] METHOD AND MATERIALS FOR CONFERRING TRIPSACUM GENES IN MAIZE

[76] Inventor: Mary Wilkes Eubanks, 4110 Hulon Dr., Durham, N.C. 27705

[*] Notice: The term of this patent shall not extend beyond the expiration date of Pat. No. PP6,906.

[21] Appl. No.: 524,113

[22] Filed: Aug. 22, 1995

Related U.S. Application Data

[63] Continuation of Ser. No. 248,333, May 24, 1994, abandoned, which is a continuation of Ser. No. 944,389, Sep. 14, 1992, Pat. No. 5,330,547, which is a continuation-in-part of Ser. No. 613,269, Nov. 13, 1990, Pat. No. Plant 7,977, and Ser. No. 117,096, Nov. 4, 1987, Pat. No. Plant 6,906.

[51] Int. Cl.⁶ .............................. A01H 1/02; A01H 5/00; A01H 5/10
[52] U.S. Cl. .......................... 800/200; 47/58; 47/DIG. 1; 435/410; 435/412; 800/250; 800/DIG. 56
[58] Field of Search ...................... Plt./100; 47/58.03, 47/58, DIG. 1; 435/240.4, 240.5, 410, 412; 800/200, DIG. 56, 250

[56] References Cited

U.S. PATENT DOCUMENTS

| P.P. 6,906 | 7/1989 | Eubanks | Plt./100 |
|---|---|---|---|
| P.P. 7,977 | 9/1992 | Eubanks | Plt./100 |
| 4,659,668 | 4/1987 | Sondahl et al. | 435/240.5 |
| 4,677,246 | 6/1987 | Armond et al. | 800/200 |
| 5,330,547 | 7/1994 | Eubanks | 800/200 |

OTHER PUBLICATIONS deWet (1979) Proc. Conf. Broadening Genet. Base Crops, Wageninger, 1978, pp. 203–210.
J.M.J. de Wet, *Tripsacum introgression and agronomic fitness in maize* (Zea Mays L.), Proc. Conf. Broadening Genet. Base Crops. pp. 203–210 (1979).
*Corn, Its Origin Evolution and Improvement*, Margelsdorf, Paul C. Belknap Press of Harvard University Press, Cambridge, MA, 1974, p. 70.

Primary Examiner—Douglas W. Robinson
Assistant Examiner—Amy J. Nelson

[57] ABSTRACT

There is provided a method for transferring Tripsacum nuclear and cytoplasmic genes into maize. The method is via a hubrid plant designated Tripsacorn (proposed botanical classification *Zea indiana*), produced by crossing two wild relatives of corn, Tripsacum and diploid perennial teosinte (*Zea diploperennis*). This invention thus relates to the hubrid seed, the hybrid plant produced by the seed and/or tissue culture, variants, mutants, and modifications of Tripsacorn and the hybrid seed, the hybrid plant produced by the seed and/or tissue culture, variants, mutants, and modifications of (maize X Tripsacorn) and/or (*Tripsacorn X maize*). In particular this invention is directed to the ability to confer rootworm resistance, resistance to insect pests, resistance to diseases, drought tolerance, and improved standability to maize via Tripsacorn.

11 Claims, No Drawings

METHOD AND MATERIALS FOR CONFERRING TRIPSACUM GENES IN MAIZE

RELATED PATENTS

This is a continuation of application Ser. No. 08/248,333 filed on 24 May 1994, now abandoned which is a continuation of Ser. No. 07/944,389 filed 14 Sep. 1992, issued as U.S. Pat. No. 5,330,547 which is a Continuation-in-part of Ser. No. 07/613,269 filed 13 Nov. 1990 issued as Plant U.S. Pat. No. 7,977, and a continuation-in-part of application Ser. No. 07/117,096, filed Nov. 4, 1987, issued as Plant U.S. Pat. No. 6,906.

FIELD OF THE INVENTION

This invention relates generally to the field of plant breeding. More particularly, it relates to a method for the production of inbred and hybrid corn with desirable characteristics including corn rootworm resistance, resistance to insect pests, resistance to diseases, drought tolerance and improved standability conferred by Tripsacum introgression via a bridge species called Tripsacorn.

BACKGROUND OF THE INVENTION

Plant breeding is the science that utilizes crosses between individuals with different genetic constitutions. The resulting recombination of genes between different lines, species or genera produces new hybrids from which desirable traits are selected. Methods employed to develop new varieties or species depend on whether a crop plant reproduces sexually or asexually. Since maize is a sexually reproducing plant, techniques for controlled pollination are frequently employed to obtain new hybrids.

A significant technological breakthrough in maize breeding was the discovery that crossing inbred lines resulted in a hybrid with greatly enhanced vigor. Inbred lines are obtained from self-pollination and selection of homozygous plants for several generations until a pure line descended by self-pollination from an apparently true-breeding plant is obtained. The purpose of inbreeding is to fix desirable characters in a homozygous condition in order that the line may be maintained without genetic change. Inbred lines with desired traits are then crossed to produce commercial hybrids. Yields from hybrid maize seed are much greater than average yields of inbreds and open-pollinated varieties.

Maize is a monoecious grass, i.e. it has separate male and female flowers. The staminate, i.e. pollen-producing, flowers are produced in the tassel and the pistillate or female flowers are produced on the shoot. Pollination is accomplished by the transfer of pollen from the tassel to the silks. Since maize is naturally cross-pollinated, controlled pollination, in which pollen collected from the tassel of one plant is transferred by hand to the silks of another plant, is a technique used in maize breeding. The steps involved in making controlled crosses and self-pollinations in maize are as follows: (1) the ear emerging from the leaf shoot is covered with an ear shoot bag one or two days before the silks emerge to prevent pollination; (2) on the day before making a pollination, the ear shoot bag is removed momentarily to cut back the silks, then is immediately placed back over the ear; (3) on the day before making a pollination, the tassel is covered with a tassel bag to collect pollen; (3) on the day of pollination, the tassel bag with the desired pollen is carried to the plant for crossing, the ear shoot bag is removed and the pollen dusted on the silk brush, the tassel bag is then immediately fastened in place over the shoot to protect the developing ear.

Wild relatives of crop plants are an important source of genetic diversity and genes well adapted to many different stresses. The wild relatives of maize include annual teosinte (*Zea mexicana*), perennial teosinte and Tripsacum. *Zea diploperennis* (hereafter referred to as *diploperennis*), is a diploid perennial teosinte. A previously unknown wild relative of maize, it was discovered on the verge of extinction in the mountains of Jalisco, Mexico in 1979. *Diploperennis*, like annual teosinte, is in the same genus as maize, has the same chromosome number (n=10), and hybridizes naturally with it. Tripsacum is a more distant relative of maize with a different haploid chromosome number (n=18). The progeny of (maize × Tripsacum) obtained by artificial methods are all male sterile and have limited female fertility when pollinated by maize pollen. Cytogenetic studies of maize-Tripsacum hybrids show partial chromosome pairing and homology between segments of Tripsacum and maize chromosomes (Maguire 1961, 1963; Chaganti 1965; Galinat 1974). In spite of strong cross-incompatibility, the fact that maize and Tripsacum chromosomes can occasionally pair enables limited transfer of Tripsacum genes into maize. Attempts to make the corollary cross, i.e. between Tripsacum and teosinte, however, have heretofore failed to produce viable plants (Tantravahi 1968; deWet and Harlan 1978).

Plant breeders acknowledge Tripsacum has significant potential for improving corn by expanding its genetic diversity (Galinat 1977; Cohen and Galinat 1984; Poehlman 1986). The limited fertility of maize-Tripsacum hybrids presents a significant biological barrier to gene flow between these species. Successful introgression of Tripsacum genetic material into maize heretofore has required years of complicated, high risk breeding programs that involve many backcross generations to stabilize desirable Tripsacum genes in maize. According to Kindiger and Beckett: "Tripsacum may be expected to contain valuable agronomic characters that could be exploited for the overall improvement of maize ... An effective procedure to transfer Tripsacum germ plasm into maize has been needed by maize breeders and geneticists for many years" (1990, p. 495). Beneficial traits that may be derived from Tripsacum include heat and drought tolerance (Reeves and Bockholt 1964), elements of apomixis, increased heterosis (Reeves and Bockholt 1964; Cohen and Galinat 1984), resistance to corn root worm (Branson 1971), corn leaf aphid (Branson 1972), northern and southern leaf blight, common rust, anthracnose, fusarium stalk rot and Stewart's bacterial blight (Bergquist 1977, 1981; deWet 1979).

(*Zea mays* × Tripsacum) plants have unreduced gametes with 28 chromosomes, one set of 10 Zea chromosomes and one set of 18 Tripsacum chromosomes. There has been one report of a successful reciprocal cross of Tripsacum pollinated by maize in which embryo culture techniques were used to bring the embryo to maturity. The plants were sterile (Farquharson 1957). This (Tripsacum × maize) plant was employed by Branson and Guss (1972) in tests for rootworm resistance in maize-Tripsacum hybrids. When the (maize × Tripsacum) hybrid has been crossed with either annual teosinte or *diploperennis*, a trigenomic hybrid has been produced that has a total of 38 chromosomes; 10 from maize, 18 from Tripsacum and 10 from teosinte. The resulting trigenomic plants were all male sterile and had a high degree of female infertility (Mangelsdorf 1974; Galinat 1986).

Transformation, a technique from molecular biology, now offers opportunity for the asexual transfer of genes that heretofore could only be achieved by crossing different plant strains. In order for breeders to employ gene transfer via transformation, they first have to be able to achieve plant regeneration from calli or protoplasts. Although transformation has been successfully performed in maize (Gordan-Kamm et al. 1990), there is limitation in developing transgenic maize due to the difficulties of plant regeneration from maize protoplasts (Potrykus 1990). The problem is there are very few maize lines that can be successfully regenerated from maize protoplasts. In order for transformation to be useful for commercial hybrid seed production, it will be necessary to have inbred lines amenable to the transgenic process that can be regenerated by tissue culture.

Rootworms, Diabrotica spp., are a serious agricultural pest. Reduction in corn yields due to corn rootworm damage ranges from 13 to 16 bushels per acre which is approximately 10 to 13%. Costs of insecticide treatments and crop losses are estimated at $1 billion per year (Metcalfe 1986). Rootworm larvae feed on the root system of corn for several weeks passing through three instars. This is the most destructive stage and causes reduced yields through damage to the root system or indirectly from lodging which makes plants difficult to harvest. Adult beetles feed on the aerial parts of the corn plant including the pollen, silks and leaves (Branson et al. 1975).

Zea diploperennis is an acceptable larval host for several Diabrotica species. Feeding scars and leaf damage have been recorded for plants growing in the wild in Jalisco, Mexico, and laboratory screening revealed diploperennis has no antibiotic effect on rootworm larvae (Branson and Reyes 1983). Tripsacum dactyloides, however, has been shown to exhibit a high degree of resistance to corn rootworm (Branson 1971). Screening of intergeneric hybrids between T. dactyloides and Zea mays showed (maize × Tripsacum) was susceptible; whereas, (Tripsacum × maize) exhibited resistance (Branson and Guss 1972). The authors proposed two explanations: (1) resistance is inherited through the cytoplasm, or (2) the genes for resistance occur on lost Tripsacum chromosomes in (maize × Tripsacum) plants.

Polyploidy refers to all natural and induced variations in chromosome number. Many cultivated crop species have evolved in nature as polyploids. One way polyploid plants arise is by combining chromosome sets from two or more species which is referred to as allopolyploidy. An allopolyploid, i.e. a plant in which the total chromosome complement of two other species is combined to form a fertile species hybrid, is referred to as an amphiploid. A plant breeding method to transfer genes across a barrier of reproduction isolation is via bridging species derived from an amphiploid. This type of introgressive hybridization produces convergence between previously more distinct species. It may result in the appearance of types that are new species intermediate to their more divergent and distinct parents. Bridging species derived from crosses between two parents with different chromosome numbers are frequently characterized by a new chromosome number. The change in chromosome complement and/or rearrangements in chromosome structure may overcome the inability of chromosomes to pair that causes infertility and often prevents the success of wide crosses.

Two wild grasses, Zea diploperennis and Tripsacum dactyloides have been crossed to produce a novel hybrid referred to as Tripsacorn, proposed botanical name Zea indiana. A bridging mechanism to transfer Tripsacum genes into maize is provided by Tripsacorn which is cross-fertile with maize. It promises to improve corn by imparting numerous beneficial characteristics including pest resistance and drought tolerance.

Based on proposed taxonomic relationships between Zea and Tripsacum and the results of prior crosses between them, the success of the crosses between Zea diploperennis and Tripsacum resulting in fully fertile plants with chromosome numbers of 2n=20 and 2n=18 could not have been predicted. The reduction in chromosome number in the interspecific cross is unexpected based on prior art. The fertility of plants resulting from the cross made both ways is also unexpected. Tripsacum and diploperennis have chromosomes that are very similar architecturally in length and their diminutive, terminal knobs that appear at one or both ends of many of the chromosomes in both species. The small terminal knobs in these species are distinct from the large internal knobs that characterize the chromosomes of corn and annual teosinte. As evidenced by cross fertility and chromosome number, the similarities in the chromosome structure of Tripsacum and diploperennis evidently promote a greater degree of pairing and enable the unexpected success of this cross.

The unexpected fertility of this hybrid, and its cross-fertility with maize, is of great value because it conveys opportunity for directly crossing with maize. Tripsacorn provides a mechanism for importing Tripsacum genes into maize in one generation by natural breeding techniques. Since Tripsacum is the female parent in this cross, it provides unique opportunity for transferring Tripsacum cytoplasmic genes into maize.

Insect resistance derived from crossing Tripsacorn with maize has been demonstrated experimentally. In a series of bioassays, seedlings from (maize ×Tripsacorn) infested with western corn rootworm, Diabrotica virgifera Le Conte, showed clear evidence for rootworm resistance. This was corroborated by comparison with maize controls and (maize × Sun Dance) plants, both of which were susceptible, as indicated by considerable root damage or death.

REFERENCES

Bergquist, R. R. 1977. Techniques for evaluation of genetic resistance in corn. North Central Regional Corn and Sorghum Disease Project, Chicago.

Bergquist, R. R. 1981. Transfer from Tripsacum dactyloides to corn of a major gene locus conditioning resistance to Puccinia sorghi. Phytopathology 71:518–520.

Branson, T. F. 1986. Larval feeding behavior and host-plant resistance in maize. In J. L. Krysan and T. A. Miller (ed.) Methods for the Study of Pest Diabrotica. Springer Verlag, New York.

Branson, T. F. and P. L. Guss. 1972. Potential for utilizing resistance from relatives of cultivated crops. Proc. North Central Branch Entomol. Soc. Am. 27:91–95.

Branson, T. F., P. L. Guss, J. L. Krysan and G. R. Sutter. 1975. Corn rootworms: Laboratory rearing and manipulation. U.S. Dept. Agric., ARS-NC-28. 18 pp.

Branson, T. F. and J. Reyes R. 1983. The association of Diabrotica spp. with Zea diploperennis. J. Kan. Entomol. Soc. 56:97–99.

Chaganti, R. S. K. 1965. Cytogenetic studies of maize-Tripsacum hybrids and their derivatives. Harvard Univ. Bussey Inst., Cambridge, Mass.

Cohen, J. I. and W. C. Galinat. 1984. Potential use of alien germplasm for maize improvement. Crop Sci. 24:1011–1015.

DeWet, J. M. J. 1979. Tripsacum introgression and agronomic fitness in maize (Zea mays L.). Proc. Conf. Broadening Genet. Base Crops, Puduc, Wageningen.

DeWet, J. M. J. and J. R. Harlan. 1978. Tripsacum and the origin of maize. In D. B. Walden (ed.) Maize Breeding and Genetics, John Wiley & Sons, New York.

Eiseman, L. and L. Herbert. 1990. *The Pantone Book of Color.* Harry N. Abrams, Inc., Publishers, New York.

Farquharson, L. I. 1957. Hybridization of Tripsacum and Zea. J. Heredity 48:295–299.

Galinat, W. C. 1974. Intergenomic mapping of maize, teosinte and Tripsacum. Evolution 27:644–655.

Galinat, W. C. 1977. The origin of corn. In G. F. Sprague (ed.). Corn and Corn Improvement. Amer. Sco. Agronomy, Madison, Wis.

Galinat, W. C. 1982. Maize breeding and its raw material. In W. L. Sheridan (ed.) Maize for Biological Research. University Press, Grand Forks, N.D.

Galinat, W. C. 1977. The origin of corn. In G. F. Sprague (ed.). Corn and Corn Improvement. Amer. Soc. Agronomy, Madison, Wis.

Galinat, W. C. 1982. Maize breeding and its raw material. In W. L. Sheridan (ed.) Maize for Biological Research. University Press, Grand Forks, N.D.

Galinat, W. C. 1986. The cytology of the trigenomic hybrid. Maize Genetics Newsletter 60:133.

Gordon-Kamm, W. 1990. Transformation of maize cells and regeneration of fertile transgenic plants. Plant Cell 2:603.

Hills, T. M. and D. C. Peters. 1971. A method of evaluating postplanting insecticide treatments for control of western corn rootworm larvae. J. Econ. Entomol. 64:764–765.

Iltis, H. H., J. Doebley, R. Guzman M. and B. Pazy. 1979. *Zea diploperennis* (Gramineae): A new teosinte from Mexico. Science 203:186–188.

Kindiger, B. and J. B. Beckett. 1990. Cytological evidence supporting a procedure for directing and enhancing pairing between maize and Tripsacum. Genome 33:495–500.

Maguire, M. P. 1961. Divergence in Tripsacum and Zea chromosomes. Evolution 15:393–400.

Maguire, M. P. 1963. Chromatid interchange in allodiploid maize-Tripsacum hybrids. Can. J. Genet. Cytol. 5:414–420.

Mangelsdorf, P. C. 1974. Corn: Its origin, evolution and improvement. Harvard Univ. Press, Cambridge, Mass.

Metcalfe, R. L. 1986. Foreword. pp.vii–xv. In J. L. Krysan and T. A. Miller (ed.) Methods for the Study of Pest Diabrotica. Springer Verlag, N.Y.

Poehlman, J. M. 1986. Breeding Field Crops. 3rd ed. AVI Publ. Co., Inc., Westport, Conn.

Potrykus, I. 1990. Gene transfer to cereals: An assessment. Biotechnology:535–542.

Reeves, R. G. and A. J. Bockholt. 1964. Modification and improvement of a maize inbred by crossing it with Tripsacum. Crop Sci. 4:7–10.

Tantravahi, 1968. Cytology and crossability relationships of Tripsacum. Harvard Univ. Bussey Inst., Cambridge, Mass.

SUMMARY OF THE INVENTION

In one embodiment of the invention, there is provided a method for conferring Tripsacum nuclear and cytoplasmic genes in maize. In the first step of the method, *Tripsacum dactyloides* (female) is crossed by *Zea diploperennis* (male) by controlled pollination technique. The resulting intergeneric hybrid derived in step 1 is fully fertile and cross-fertile with maize. It is characterized by its utility as a genetic bridge to transfer Tripsacum genes into corn.

In another embodiment of the invention, the intergeneric (*Tripsacum dactyloides* × *Zea diploperennis*) hybrid plant derived from step 1, referred to as Tripsacorn, and maize are crossed by controlled pollination. This invention relates to the hybrid seed, the hybrid plant produced by the seed and/or tissue culture, variants, mutants, and modifications of Tripsacorn, of (maize × Tripsacorn) and of (Tripsacorn × maize).

In another embodiment of the invention, there is provided plants and plant tissues produced by the method of crossing maize (female) by Tripsacorn (male) which exhibit resistance to rootworm.

In another embodiment of the invention, there is provided plants and plant tissues produced by the method of crossing maize (female) by Tripsacorn (male) which exhibit tolerance to drought.

In another embodiment of the invention, there is provided plants and plant tissues produced by the method of crossing maize (female) by Tripsacorn (male) which exhibit enhanced resistance to disease.

In another embodiment of the invention, there is provided plants and plant tissues produced by the method of crossing maize (female) by Tripsacorn (male) which exhibit enhanced resistance to insect pests.

In another embodiment of the invention, there is provided plants and plant tissues produced by the method of crossing maize (female) by Tripsacorn (male) which exhibit resistance to lodging.

For the purposes of this application, the following terms are defined to provide a clear and consistent description of the invention.

Allopolyploid. An individual with two or more chromosome sets.

Amphiploid. An individual with two or more genomes derived from different species.

Antibiosis. Antibiosis refers to the plant's ability to adversely effect the insect pest, for example by producing a toxic substance.

Antixenosis. Antixenosis refers to the plant's ability to detract the insect pest away from the plant, for example by producing a deterrent substance.

Hybrid plant. An individual plant produced by crossing two parents of different genotypes.

Polyploid. An individual with some variation in normal diploid chromosome number.

Root Lodging. Root lodging is indicated when plants lean from the verticle axis an at angle $\geq 30°$.

Tolerance. Tolerance is indicated when a plant sustains rootworm damage but is still able to grow in spite of damage.

DETAILED DESCRIPTION OF INVENTION

The method of the invention is performed by crossing *Tripsacum dactyloides* and *Zea diploperennis*. The crosses are performed using standard plant breeding techniques for controlled pollinations known in the art.

Thus, the present invention provides a method of producing hybrid plant seeds comprising the steps of (a) crossing a Tripsacum species (e.g. *Tripsacum dactyloides*) female parent with a Zea species (e.g. *Zea diploperennis*) male parent to produce seed; then (b) harvesting the seed produced.

This method produces a hybrid seed and a hybrid plant, from which tissue cultures can be made. Additionally, pollen produced by the hybrid plant can be collected.

The term "plant" as used in this application refers to the whole plant as well as its component parts, e.g., flowers, roots, fruits, and rhizomes.

The present invention further provides a method of producing hybrid corn seed comprising the steps of (a) crossing a *Tripsacum dactyloides* female parent with a *Zea diploperennis* male parent to produce (*Tripsacum dactyloides* × *Zea diploperennis*) hybrid seed; then (b) growing a (*Tripsacum dactyloides* × *Zea diploperennis*) hybrid plant from said seed to maturity; then (c) crossing said (*Tripsacum dactyloides* × *Zea diploperennis*) hybrid plant with maize to produce seed and (d) harvesting the seed produced.

This method results in the production of hybrid corn seed and hybrid corn plants, from which tissue cultures can be made. One marked benefit of the present invention is the production of hybrid corn plants which exhibit enhanced resistance to corn rootworm.

Plant breeding techniques and tissue culture techniques as described herein are known, and may be carried out in the manner known to those skilled in the art. See, for example, U.S. Pat. No. 4,737,596 to Seifert et al. entitled "Hybrid Corn Plant and Seed"; U.S. Pat. No. 5,059,745 to Foley entitled "Hybrid Corn Line LH195"; U.S. Pat. No. 4,545,146 to Davis entitled "Route to Hybrid Soybean Production"; U.S. Pat. No. 4,627,192 to Fick entitled "Sunflower Products and Methods for their Production", and U.S. Pat. Nos. 4,837,152 and 4,684,612 entitled "Process for Regenerating Soybeans". Applicant specifically intends that the disclosure of all U.S. patents cited herein be incorporated herein by reference.

In Tripsacum inflorescences, the staminate (i.e. male) flowers and pistillate (i.e. female) flowers are produced on a single spike with the male flowers subtended by the female. When Tripsacum sends out the inflorescence, the staminate flowers are broken off leaving only the female flowers on the spike which is then covered with a pollinating bag, i.e. standard ear shoot bag for maize, to protect them from contamination by unwanted pollen. *Diploperennis* male and female flowers occur on separate parts of the plant. The staminate flowers are borne in the tassel which emerges at the apex of the culm; whereas, the pistillate flowers occur in single-rowed spikes borne on lateral branches of the culm. When *diploperennis* produces its tassels, they are covered with a pollinating bag. When they start shedding pollen, the bag is removed and pollen taken to pollinate the Tripsacum plants. At that time, the bags covering the Tripsacum pistillate flowers are removed and the *diploperennis* pollen shaken out of the bag onto the silks. The Tripsacum inflorescence is covered again with a pollinating bag immediately after pollination and the bag is stapled so that it remains on the spike until the seed has matured. Upon maturity, approximately 45 days later, the seed is harvested. Once mature seed from the cross has been obtained, it is germinated on moist filter paper in a petri dish in the dark. When the seed starts to germinate, it is transferred to potting soil in a pot. The plants are grown in the greenhouse or outdoors. Controlled crosses are best made in a greenhouse where plants are kept isolated to prevent cross contamination and there is no problem with bags being damaged by weather conditions.

This method may alternatively be used to cross the plants with *diploperennis* as the female parent. In this embodiment, all the tassels, i.e. male flowers, are removed from the *diploperennis* plant as soon as they emerge and the ears, i.e. female flowers, are covered with pollinating bags. Rather than removing Tripsacum male flowers, the spikes are left intact and covered with a pollinating bag to collect Tripsacum pollen. The pollen is applied to the *diploperennis* ears which are then immediately covered with a pollinating bag that is well fastened with staples to ensure it remains sealed until the seed has matured, approximately 45 days after pollination when the seed is harvested.

Next, when (Tripsacum × *diploperennis*) starts to flower, the same steps described above are used to cross the hybrid with maize. To cross onto maize, as soon as the maize plants begin to produce ears, before the silks emerge, the ears are covered with an ear shoot bag. Pollen collected from (Tripsacum × *diploperennis*) is applied to silks of the maize ears. The ears are then covered again with an ear shoot bag and a large pollinating bag which is wrapped around the culm and secured with a staple. The ears remain covered until they reach maturity, several weeks later when the ears are harvested.

Plants grown from all crosses described above are male and female fertile and are cross-fertile with each other.

The principles and techniques used in breeding insect and disease resistance are basically the same. First, sources of resistance genes must be located. Secondly, genes for resistance must be transferred into adapted varieties by hybridization procedures, and thirdly, those varieties must be exposed to the insect pest or disease under natural or artificially induced conditions in order to distinguish resistant strains from susceptible strains. The mode of inheritance of resistance may be simple and involve only one to two major genes. Though in most cases resistance is dominant, it may be dominant or recessive. Inheritance of resistance also may be more complex with numerous genes affecting the host-parasite relationship. Plant breeders test for resistance by experimental inoculation of plants grown in the field and/or the greenhouse. In testing for rootworm resistance, artificially reared insects are transferred to plants grown in the field or a greenhouse, or to newly germinated seedlings in petri dishes. The infected plants are observed and evaluated according to specific criteria for a particular pest. In looking for rootworm resistance, criteria for evaluation include observations of plant lodging and scoring of root damage by a standardized scale.

Tripsacum × *dipoloperennis*

A detailed description of the plants obtained from (Tripsacum × *diploperennis*) is outlined below.

Origin: Seedling

Parentage:

Seed parent.—*Tripsacum dactyloides*

Source: Established clone at Indiana University, Bloomington, Ind.

Pollen parent.—*Zea diploperennis*

Source: Jalisco, Mexico (Reference Iltis et al., 1979)

Classification: Botanic—*Zea indiana* (proposed).

Cytology: Diploid chromosome number determined from root tips ranged from 2n=18 to 2n=20.

Habit: Essentially erect; as many as 35 primary culms, usual number about 15.

Duration:

Perennial.—Sends out shoots from rhizomes. Plant will freeze at winter temperatures below 28° F., but new growth is produced in spring after winter temperatures of 0° F.

Culm:
  Height.—Up to two meters: slender, simple with occasional branching from the nodes of the culm; glabrous; oval in cross section; diameter 1–1.2 cm.
  Nodes.—glabrous, aerial roots develop at nodes along culm.
  Sheath.—tightly closed enwrapping the culm, margins not united; glabrous; turns rose red (Pantone #18-1852) when exposed to sun, otherwise green; rose red (Pantone #18-1852, ciliate auricles at summit margins.
  Ligule.—present on adaxial side of leaf at junction of blade and sheath; length: 4 mm; membranaceous, irregular edge.
Leaf blade: Alternate; distichous; sheathing base; parallel veined; narrowly linear, flat, thin.
  Length.—47–56 cm. Width: 1.5–5.0 cm.
  Entire margin.—Rose red (Pantone #18-1852), serrulate.
  Midrib.—White (Pantone #12-5202).
  Adaxial surface.—Sparsely hirsute.
  Abaxial surface.—Glabrous except sparsely hirsute along midrib.
  Prominent parallel veins.—5 per 1 cm width.
Inflorescence
  Blooming period: Twice annually in the greenhouse for approximately one month beginning in late April and late October in Tennessee, North Carolina and Mississippi.
  Monoecious: Separate male and female flowers on the same plant; variable.
  Staminate flowers: May be of two types: one inflorescence type borne as paired spikelets on a slender rachis forming 3–7 racemes arranged in a panicle, the "tassel", at the summit of the culm. Alternatively, staminate spikelets may be borne on a single spike above the pistillate flowers.
    Length.—6–12 cm.
    Axis.—stiff, continuous, ascending.
  Spikelet: Two-flowered, one sessile, one pedicled; laterally compressed awnless, attenuate with red (Pantone #19-1860) tip and red (Pantone #19-1860) band at base; Length: 11 mm;
  Width: 3 mm. In pairs on one side of a persistent central axis.
    Pedicel length.—3 mm.
    Glumes.—Outer glume: cartilaginous, tapering to an acute tip, ciliate, flat, several nerved, margins involute, fimbriate.
    Inner glume: chartaceous.
    Pistillate flowers: Borne in leaf axils; spikelets distichously arranged; variable.
    Styles: pilose with distinct bifurcated tips.
    Color: Ranges from pastel parchment (Pantone #11-0603) to light lilac (Pantone #12-2903) to rose red (Pantone #18-1852).
  Length: 100 mm.
  One type of pistillate flower consists of a single rowed spike of 4 to 6 triangular caryopses in hard, shell-like fruitcases enclosed in a single leaf sheath; caryopses disarticulate upon maturity.
    Length: 7.5 mm; Width: 5 mm.
    Colors range from solid to variegated combinations of the following: White (Pantone #11-0602), gray (Pantone #16-1107), tobacco brown (Pantone #17-1327), brown (Pantone #19-1121), dark brown (Pantone #19-1020).

Alternatively, spikelets paired and partially enclosed in stiff, brown speckled glumes; caryopses rounded and imbricate; Spikes enclosed in single or multiple leaf sheaths. Caryopses do not disarticulate upon maturity;
  Length: 5 mm; Width: 5 mm.
  Color variegated combinations of the following: dark brown (Pantone #19-1217, brown (Pantone #18-1154), beige (Pantone 15-1225), light beige (Pantone #13-1018).
  Fruit: Five to ten ears per culm per blooming period; flowers are produced twice a year under greenhouse conditions; some plants may produce approximately 150 ears twice annually.
  Maturity: 45 days following fertilization.
  Ear (Husked Ear Data Unless Stated Otherwise)
  Length: About 43 mm.
  Midpoint diameter: About 6.7 mm.
  Weight: 0.5 gm.
  Kernel rows: 2 (rarely 3–4)
  Silk color (exposed at silking stage): light lilac (Pantone #12-2903) to rose red (Pantone #18-1852).
  Husked color: Cob kernels are embedded in the rachis segments, some of which disarticulate upon maturity. These segments are brownish gray and are the hard, bony fruitcases enclosing the kernels.
  Kernel color: beige (Pantone #14-1122) shading to golden beige (Pantone #16-1336).
  Husked extension (harvest stage): About 1 cm.
  Shank: About 6.5 cm.
  Taper: Slight.
  Position in dry husk stage: Upright.
  Drying time (unhusked ear): About 2–3 days.
  Kernel (Dried)
  Type I: Angular caryopses in hard, shell-like fruitcases, disarticulate upon maturity:
    Size (from midpoint): Length about 0.8 mm, width about 0.5 mm, thickness about 0.4 mm.
    Shape: Trapezoidal
    Colors range from solid to variegated combinations of the following: white (Pantone #11-0602), gray (Pantone #16-1107), tobacco brown (Pantone #17-1327), brown (Pantone #19-1121), dark brown (Pantone #19-1020)
    Weight 20 seeds (unsized samples): 1.3 gm.
  Type II: Paired caryopses partially enclosed in endurated glumes forming a cob, upon maturity do not disarticulate:
    Size (from midpoint): Length about 3.9 mm, width about 2.8 mm, thickness about 2.7 mm.
    Shape grade (% round): 100% round (tip pointed).
    Pericarp color: beige (Pantone #14-1122) shading to golden beige (Pantone #16-1336).
    Aleurone color: Clear.
    Endosperm color: White (Pantone #11-0601).
    Endosperm type: Pop.
    Weight 20 seeds (unsized samples): About 0.4 gm.
  Cob
  Diameter at midpoint: 5.3 to 8.7 mm.
  Strength: Variable.
  Color: Smoke (Pantone #12-0704).
  Alicole: Length: About 6.6 mm.
    External width: 7.0 mm. Internal width: 5.0 mm.
    External length: 5.5 mm. Internal length: 5.0 mm.

Thickness: Approximately 4.5 mm. Depth: 2.9 mm.

Cupule: Overhang: About 0.6 mm. Wing height: 4.1 mm. Left wing width: 1.0 mm. Right wing width: 1.3 mm. Lower glume length: 5.9 mm. Lower glume width: ~3.0 mm.

Lower glume angle: ~20°. Glume cushion width: 5.4 mm.

Glume cushion height: 1.8 mm. Sessile thickness: 0.3 mm.

Cupule pubescence: sparse, short hairs.

Color: Buff (Pantone #13-1024).

Comparative Parental Characteristics

Duration: Z. diploperennis does not survive temperatures below approximately 24° F. T. dactyloides is a true perennial and produces new growth every year surviving temperatures are below 0° F.

Leaf blade: Zea diploperennis round in cross section; diam. 1 cm. Tripsacum dactyloides oval in cross section; diam. 1.3 cm.

Leaf blade: Z. diploperennis. Width 1–2 cm; margins pink serrulate from midsection of blade to tip; adaxial surface: sparsely hirsute; prominent veins: 6 per 1 cm width. T. dactyloides.

Width: 1 cm; margins white serrulate along entire blade; Adaxial surface: hirsute; prominent veins: 12 per 1 cm.

Blooming period: Z. diploperennis twice a year in the greenhouse, end of March and end of September for about a month. T. dactyloides continuously from May to October.

Staminate flowers: Z. diploperennis borne in tassel at summit of culm. T. dactyloides staminate flowers borne above pistillate flowers in single spike.

Pistillate flowers: Z. diploperennis caryopsis triangular-trapezoidal in hard bony fruitcases; Length: 8 mm; Width: 4–5 mm; Color: black (Pantone #19-0303), dark brown (Pantone #19-1020) or mottled black-brown. T. dactyloides caryopsis trapezoidal in hard, bony fruitcase; Length: 6–10 mm; Width: 6 mm. Color: pale brown (Pantone #17-1137) or buff (Pantone #13-1024).

Maize × Tripsacorn (Maize × Tripsacorn) plants look basically like maize. One difference when comparing these plants to maize controls is that they are shorter, have stronger stalks and are not susceptible to lodging. The ears look like maize and are equal in weight to maize ears. However, the kernels tend to be larger in size than kernels of maize controls. The plants produced by (maize × Tripsacorn) do not show as many signs of infestation by insects or disease as maize controls. Noticeable resistance to aphids and white flies has been observed on plants grown in the greenhouse and enhanced resistance to corn earworm and ear and kernel rot has been observed in plants grown in the field. Laboratory bioassays have shown enhanced resistance to corn rootworm. When subjected to dry conditions, (maize × Tripsacorn) plants do not exhibit signs of wilting and drought stress to the same extent as maize controls.

EXAMPLES

Bioassays for Determining Rootworm Resistance in Maize

Two types of bioassays, in petri dishes and in pots, were conducted to determine if Tripsacorn could impart rootworm resistance to maize. For the bioassays, 1,000 non-diapausing western corn rootworm eggs in soil were shipped from French Agricultural Research, Inc., Lamberton, Minn., to Durham, N.C., under U.S. Department of Agriculture permit number 922762. Plants were infested with newly hatched first instar larvae of western corn rootworm, Diabrotica virgifera. The larvae were transferred to test containers by lifting with a small paint brush. Two separate petri dish bioassays and three pot bioassays were performed.

For the bioassays, seed from Tripsacorn crossed to four diverse types of maize was used. The four types included: a commercial hybrid corn seed Funk's G4522; two inbred lines, B73 and W64A; a native Mexican race, Zapalote Chico, classified as a prehistoric mestizo indicating derivation from ancient indigenous races. Other plants infested with corn rootworm included (G4522 × Sun Dance), Tripsacum, Tripsacorn and maize controls.

Petri Dish Bioassays

Petri dish bioassays were employed to screen for antibiosis versus antixenosis by observing whether larvae remained on the roots, ate them and survived or died; or whether larvae moved away from the roots. If there is an antibiotic effect, evidence for eating and dead larvae can be seen; if there is an antixenotic effect, larvae can be observed trying to leave the dish. For these tests, 10 grams of top soil sieved through a 1 mm mesh screen was placed in a petri dish with 3 to 5 freshly germinated seedlings or, in the case of Tripsacum, with a small clonal piece of plant with young roots, and kept moist. The rims of each dish were ringed with petroleum jelly to monitor for any larvae trying to leave the dish. Up to a total of 50 larvae were added to each dish over a three day period. Each treated dish was observed for several days under a dissecting microscope at 60× magnification and behavior recorded.

The plants used in the petri dish bioassays and observed results are summarized in Table I. In all cases, larvae remained on or near the roots, seed and cotyledons or in the soil. There was no indication of larvae trying to exit the petri dishes and thus, it is concluded no evidence for antixenosis. Tripsacum, Tripsacorn, (B73 × Tripsacorn), (W64A × Tripsacorn), (G4522 × Tripsacorn) and (G4522 × Sun Dance) did not show any signs that the roots produce a substance that is a deterrent to the insects. Larvae feeding was observed in all cases and severity of root damage rated by the Hills and Peters scale. Evidence for antibiosis and tolerance was indicated with Tripsacorn and the hybrids between corn and Tripsacorn tested; whereas, there was no evidence for antibiosis or tolerance with the corn and (maize × Sun Dance) materials tested.

TABLE I

| RESULTS OF PETRI DISH BIOASSAYS | | |
|---|---|---|
| | No. of Larvae | Observations/Comments |
| Bioassay #1 | | |
| Tripsacum | 50 | Larvae stay on root, some feeding but virtually no damage to roots, larvae not visible after a couple of days |
| Tripsacorn | 50 | Some feeding, little root damage |
| B73 X Tripsacorn | 50 | Some feeding, little root damage, plants continue to grow |
| G4522 X Tripsacorn | 50 | Some feeding, little root damage, plants |

TABLE I-continued

RESULTS OF PETRI DISH BIOASSAYS

| | No. of Larvae | Observations/Comments |
|---|---|---|
| | | continue to grow |
| G4533 X Sun Dance | 50 | Extensive feeding, plants died |
| Corn control | 50 | Extensive feeding, plants died |
| Bioassay #2 | | |
| Tripsacorn | 20 | Light feeding, some dead larvae |
| Corn control (W64A) | 45 | Extensive feeding, plants died |
| W64A X Tripsacorn | 45 | Feeding on roots, seed and cotyledons, some dead larvae |

Pot Bioassays

Plants grown in pots were used to screen for evidence of tolerance and/or antibiosis. Lodging is seen in plants that are susceptible to rootworm damage; whereas, plants that remain upright and healthy when exposed to rootworms are indicative of tolerance and antibiosis. Root damage was observed and scored according to the Hills and Peters (1971) rating scale of 1–6 that is widely used in the corn belt to evaluate root damage. The criteria for rating are as follows:

1. No damage or only a few minor feeding scars
2. Feeding scars evident but no roots eaten off to within 1½ inch of the plant
3. Several roots eaten off to within 1½ inch of the plant but never the equivalent of an entire node of roots destroyed
4. One root node completely destroyed
5. Two root nodes completely destroyed
6. Three or more root nodes destroyed When a bioassay was complete, two to three plants were removed from the pots, soaked in water then rinsed with a gentle water spray to clean the roots, then observed under a dissecting microscope for scoring. The score reported is the mean calculated from the total scores of plants in each category. Tolerant plants may suffer root damage but are capable of regrowth and degrees of plant recovery. Well developed secondary root systems are often capable of compensatory growth from damaged crown roots.

In the first pot bioassay, 3 to 5 seedlings (approximately 1 week old), or in the case of Tripsacum a small clone with young roots, were planted in potting soil in 10-ounce containers and were grown indoors under artificial grow lights. A total of 70 larvae were added to each container over a two day period and plants were observed for 11 days.

In the second pot bioassay, $\leq 10$ day old seedlings were planted in potting soil in 3 inch peat pots and grown indoors under artificial grow lights. A total of 30 larvae were added to each pot over a three day period. Although most plants were dead within one week, observation of the ones that survived extended over two weeks before plants were sacrificed for root evaluation. For each type, there were a minimum of two plants, and in most cases there were four plants.

In the third pot bioassay, the plants were 11 to 14 days old at infestation and they were grown on a porch under natural sunlight. A total of 30 larvae were added to each pot over two days. They were observed for 11 days before sacrificing plants to score root damage.

The plants used in the pot bioassays and observed results are summarized in Table II. The results indicate that (maize × Tripsacorn) plants are definitely more resistant to corn rootworm than corn controls and (maize × Sun Dance). The mechanisms indicated for resistance inherited from Tripsacorn are antibiosis and tolerance. All the plants sustained some injury to the roots. Lodging in the corn controls and (maize × Sun Dance) plants was $\geq 45°$ and rating on the Hills and Peters scale ranged from 5 to 6. The corn × Tripsacorn plants remained upright and appeared healthy, but did sustain root damage. There was good development of secondary roots from the damaged crown showing the capability for compensatory growth in all the (maize × Tripsacorn) plants.

TABLE II

RESULTS OF POT BIOASSAYS

| | No. of Larvae | Duration | Root Damage* | Observations/Comments |
|---|---|---|---|---|
| Bioassay #1 | | | | |
| Tripsacum | 70 | 11 days | Not recorded | No sign of damage |
| Tripsacorn | 70 | 11 days | Not recorded | No sign of damage |
| B73 X Tripsacorn | 70 | 11 days | Not recorded | No sign of damage |
| G4522 X Tripsacorn | 70 | 11 days | Not recorded | No sign of damage |
| G4522 X Sun Dance | 70 | 11 days | Not recorded | Plants died after 6 days |
| Bioassay #2 | | | | |
| Corn control (W64A) | 30 | 14 days | 5.0 | Plants died |
| W64A X Tripsacorn | 30 | 14 days | 2.0 | Plants weakened |
| G4522 X Sun Dance | 30 | 14 days | 5.0 | Plants died |
| Bioassay #3 | | | | |
| Corn control (Zapalote Chico) | 30 | 11 days | 4.0 | Lodging ($\geq 45°$), leaf damage |
| Zapalote Chico X Tripsacorn | 30 | 11 days | 2.0 | Minor leaf damage |
| Corn Control (W64A) | 30 | 11 days | 4.0 | Lodging ($\geq 45°$), |
| W64A X Tripsacorn | 30 | 11 days | 2.3 | Plant upright and growing |
| G4522 X Sun Dance | 30 | 11 days | 5.0 | Lodging ($\geq 45°$), leaf damage |
| Tripsacorn | 30 | 11 days | 1.0 | No evidence of damage |

*Hills and Peters scale (1971)

DEPOSIT OF SEEDS

Seeds derived from crosses between *Tripsacum dactyloides* and *Zea diploperennis* as described herein were deposited in accordance with the provisions of the Budapest Treaty with American Type Culture Collection, 12301 Parklawn Drive, Rockville, Md. 20852 on Aug. 28, 1992. The accession number is ATCC75297.

The present invention is not limited in scope by the seeds deposited, since the deposited embodiments are intended as single illustrations of one aspect of the invention and any seeds, cell lines, plant parts, plants derived from tissue culture or seeds which are functionally equivalent are within the scope of this invention. While the invention has been described in detail and with reference to specific embodiments thereof, it will be apparent to one skilled in the art that changes and modifications can be made without departing from the spirit and scope of the invention in addition to those shown and described herein. Such modifications are intended to fall within the scope of the appended claims.

I claim:

1. A method of producing hybrid plant seed comprising the steps of:
   (a) crossing a *Tripsacum dactyloides* female parent with a *Zea diploperennis* male parent, or a *Zea diploperennis* female parent with a *Tripsacum dactyloides* male parent to produce seed; and
   (b) harvesting said seed produced in (a).

2. Seed produced in accordance with the method of claim 1.

3. A hybrid plant grown from seed according to claim 2, said plant being fertile and having a diploid chromosome number of between 18 and 20.

4. Pollen produced by a plant according to claim 3.

5. A tissue culture produced from a plant according to claim 3, the cells of said tissue culture having a diploid chromosome number of between 18 and 20.

6. A method of producing hybrid maize seed comprising the steps of:
   (a) crossing a *Tripsacum dactyloides* female parent with a *Zea diploperennis* male parent to produce (*Tripsacum dactyloides* × *Zea diploperennis*) hybrid seed or crossing a *Zea diploperennis* female parent with a *Tripsacum dactyloides* male parent to produce (*Zea diploperennis* × *Tripsacum dactyloides*) hybrid seed;
   (b) growing a hybrid plant from said hybrid seed to maturity;
   (c) crossing said hybrid plant with *Zea mays* to produce seed; and
   (d) harvesting the seed produced in (c), wherein said seed germinate into plants having resistance to corn rootworm (*Diabrotica virgifera*).

7. Hybrid maize seed produced in accordance with the method of claim 6.

8. Hybrid maize plants grown from said seed of claim 7.

9. Hybrid maize plants grown from said seed of claim 7, wherein said plants exhibit resistance to corn rootworm.

10. Hybrid maize plants grown from said seed of claim 7, wherein said plants exhibit resistance to lodging.

11. A tissue culture derived from said hybrid maize plants claimed in claim 8.

* * * * *